United States Patent
Bartfeld et al.

(10) Patent No.: US 9,177,265 B2
(45) Date of Patent: *Nov. 3, 2015

(54) SYSTEM AND METHOD FOR REAL TIME IDENTIFICATION OF A DRUG

(75) Inventors: Eyal Bartfeld, Lexington, MA (US); Amir Lass, London (GB)

(73) Assignee: Irody, Inc., Boston, MA (US)

(*) Notice: Subject to any disclaimer, the term of this patent is extended or adjusted under 35 U.S.C. 154(b) by 133 days.

This patent is subject to a terminal disclaimer.

(21) Appl. No.: 12/766,748

(22) Filed: Apr. 23, 2010

(65) Prior Publication Data

US 2010/0215231 A1    Aug. 26, 2010

Related U.S. Application Data

(63) Continuation of application No. 11/744,870, filed on May 6, 2007, now Pat. No. 7,747,454.

(60) Provisional application No. 60/798,278, filed on May 6, 2006, provisional application No. 60/798,279, filed on May 6, 2006.

(51) Int. Cl.
| | | |
|---|---|---|
| G06Q 50/00 | (2012.01) |
| G06Q 10/00 | (2012.01) |
| G06F 19/00 | (2011.01) |
| G06Q 40/08 | (2012.01) |
| G06Q 50/22 | (2012.01) |
| G06Q 50/24 | (2012.01) |
| G07F 17/00 | (2006.01) |
| G07G 1/00 | (2006.01) |

(52) U.S. Cl.
CPC ............ *G06Q 10/00* (2013.01); *G06F 19/3462* (2013.01); *G06Q 40/08* (2013.01); *G06Q 50/22* (2013.01); *G06Q 50/24* (2013.01); *G07F 17/0092* (2013.01); *G07G 1/0054* (2013.01)

(58) Field of Classification Search
None
See application file for complete search history.

(56) References Cited

U.S. PATENT DOCUMENTS

| | | | | |
|---|---|---|---|---|
| 5,845,264 | A  * | 12/1998 | Nellhaus .......................... 705/28 |
| 6,421,650 | B1 * | 7/2002 | Goetz et al. ....................... 705/3 |
| 6,535,637 | B1 * | 3/2003 | Wootton et al. ............... 382/190 |
| 2005/0267356 | A1 * | 12/2005 | Ramasubramanian et al. ............................. 600/411 |
| 2006/0124656 | A1 * | 6/2006 | Popovich ........................... 221/9 |

FOREIGN PATENT DOCUMENTS

| | | | |
|---|---|---|---|
| WO | WO 0225568 A2 * | 3/2002 |
| WO | WO02081015 | * 10/2002 |

* cited by examiner

*Primary Examiner* — Michelle L Le
(74) *Attorney, Agent, or Firm* — Lawson & Weitzen LLP; Sonia K. Guterman; Anna E. Stanford (57) ABSTRACT

A system for managing a prescribed drug regimen for a user, the system including at least one electronic device (Pod) for interactive communication with at least one user, a Pod server coupled via a communication link to each Pod, said Pod server including an analysis unit, the analysis unit including a database of drug characteristics, and a processor for comparing sensed characteristics of a drug in one of the Pods with characteristics in the drug characteristics database, so as to identify the drug, and to provide to the Pod an indication of compatibility of the drug with the drug regimen.

23 Claims, 7 Drawing Sheets

SYSTEM AND METHOD FOR REAL TIME IDENTIFICATION OF A DRUG

RELATED APPLICATIONS

This application is a continuation application and claims the benefit of utility application Ser. No. 11/744,870 filed May 6, 2007, now U.S. Pat. No. 7,747,454 issued Jun. 29, 2010 which claims the benefit of Provisional Applications 60/798,278 and 60/798,279, both filed May 6, 2006 respectively, in the U.S. Patent and Trademark Office, each of which is hereby incorporated by reference herein in its entirety.

FIELD OF THE INVENTION

The present invention pertains to a system and method for identifying a drug.

BACKGROUND OF THE INVENTION

Drugs are effective in treating a wide range of diseases and medical conditions. They are designed to be consumed according to a defined protocol, which includes dosing and timing. Demand for prescription drugs is growing at a rate that exceeds the capacity and numbers of licensed pharmacists. Currently more than 200 million prescriptions are filled in the US alone every week. The number of prescriptions filled between 2000 and 2005 increased roughly by 41%, while the number of retail pharmacists increased roughly by 4.5%.

However, there are a few major problems associated with prescribed and non prescribed drugs, which create a safety risk or reduced efficacy:
1. Drug—drug interactions which occur when actually consuming the drugs
2. Medication errors made by physicians
3. Non compliance and non-adherence by patients
4. Vending errors by pharmacists
5. Drug counterfeit Errors can be made in any stage of the drug cascade: manufacturing, prescribing, dispensing and consumption. They can occur at the manufacturing site, in hospitals, pharmacies, community clinics and at home. Two in-patient studies, one in adults and one in pediatrics, have found that about half of medication errors occur at the stage of drug ordering, and direct observation studies have indicated that many errors also occur at the administration stage.

The purpose of the invention described herein is to assist patients and people who consume medications to considerably reduce the risk associated with these factors.

1. Drug-Drug Interactions:

All drugs affect multiple organs and many systems, and have different mechanisms of absorption, distribution metabolism and elimination. However, many, if not most, individuals take more than one drug at a time. Once a drug is consumed, it may alter one or more of the mechanism of action of another drug causing a reduction of efficacy or a toxic effect.

While clinicians are in general familiar with the concept of cross activities of drugs, which are mentioned in the summary of product characteristics (SmPC) and prescribing information (PI), in many cases they are unaware of specific potential interactions while prescribing a drug for one of the following reasons: The clinician is prescribing the drug only in rare cases, the drug is new on the market, the patient did not disclose all drugs he/she is taking (or was not asked about them), personal habits are not disclosed (dietary, alcohol, smoking, etc.) or the clinician or the pharmacist is not familiar with many of the possible combinations of drug interactions 2. Medication Errors Medication errors are errors in the processes of ordering, transcribing, dispensing, administering, or monitoring drugs, irrespective of the outcome (i.e. injury to the patient).

3. Non-Compliance and Non-Adherence

Non-compliance and non-adherence errors are made by the patient. The principal types of non-compliance errors are: missing a dose, incorrect drug, incorrect frequency of administration, or completely stop taking the drug 4. Vending Errors This type of errors occurs when drugs are sold by a pharmacist to the patient. Typically, these errors occur due to similar names or similar packages of drugs. A high work load on pharmacists also contributes to the error rate.

5. Drug Counterfeit

This is a growing issue where a look-alike drug, which may contain an inert or a different material, is sold on the market as if it were the original drug. The danger here is that the patient will not get the benefits of the proper drug, at all.

SUMMARY OF THE INVENTION

The present invention pertains to a system and method for managing patient care associated with a drug regimen. The purpose of the invention described herein is to assist patients and people who take medications and other drugs to considerably reduce the risk associated with the above factors.

For purposes of the present invention, the term "drug" is used to include prescription drugs and non-prescription drugs (also known as Over the Counter (OTC) drugs), food supplements, vitamins and preventive drugs.

The invention provides a system designed primarily for residential use by people who are on a drug regimen. The drug regimen includes all drugs, prescribed and not prescribed, food supplements, vitamins, and the like, taken by a person, including dosage and timing, and preferably includes an indication of allergies or sensitivities to any drugs or food supplements to be used during drug analysis. The system aims at eliminating errors associated with taking drugs, alerting users to possible adverse drug interactions and reminding users to take their drugs, thereby improving compliance with the drug regimen.

The basic system design includes an electronic client terminal device (a Pod) for interactive communication with a user, software and medical databases, preferably running in a remote computer (server or Pod Server), and communication links between the Pod and the Server.

Optional modules of the system include a client Web interface. Preferably, a drug to be identified before taking is placed in the Pod. The system performs processing on the remote server to determining compatibility of the drug with the user's drug regimen, and relays results of the analysis to the user. Preferably, based on the analysis, the Pod either releases the blocks to the user or blocks it. In the latter case, the user may override the blocking function and may also communicate with a remote service center, in one of several manners including, among others, text and voice.

Several embodiments of suitable Pods, which are capable of being associated with one or more users, are described in detail and claimed in applicants' co-pending patent application entitled: Apparatus and Method for Obtaining an Identification of Drugs for Enhanced Safety.

The remote computer server is capable of simultaneously interacting with a plurality of Pods and includes an analysis unit having databases with users' drug-taking history, users' regimen, drug data, drug interaction data, and communication hardware and software.

The communication links facilitate data, voice, and video communication between a user and the server and, in one embodiment, between users and expert consultants or a support center. Communication can be over the Internet, cellular networks, satellite links, or any other communication technologies.

The Web interface allows users to enter their drug regimen into the system, view their medication taking history, and next dose information.

The Server is capable of communicating with a plurality of Pods. Preferably, the Pods are located at consumers' premises, or may be portable devices for carrying with the user. According to one preferred embodiment of the invention, the Pods are devices capable of capturing images, and/or additional optical information or other characteristics of the drugs, other optical elements embedded in drugs or imprinted on the drugs themselves, or on their packaging.

Preferably, the server contains capabilities allowing it to actively alert and send further information to a user or users by using the Pod to display the alert. According to another preferred embodiment of the invention, the Pod may contain additional communication capabilities and input/output capabilities enabling the user to communicate with experts by using voice or data, or enabling the Pod to display video information communicated to it by the Pod Server.

According to one embodiment of the invention, the system utilizes Pods that are able to capture images or other data regarding a drug that the user is taking, and transmit the information to the Server. In a preferred embodiment, the Pod includes at least one camera, and a lighting mechanism. This allows the Pod to capture images and then send them to the Pod server. In some other embodiments, processing takes place in the Pods and they either send the processed results to the Pod server, or if they are not connected to a communication network at that particular moment, they store information of medications inside the Pod. That information may be communicated to a Pod server at a later time, when connected.

According to another embodiment of the invention, a Pod can be a cellular telephone equipped with a camera and software that enables it to send images captured by the camera to the Server.

According to a preferred embodiment of the invention, a user has one Pod and the Pod is associated with the user using identifiers, such as a hardware identification code or a telephone number. However, it should be noted that more than a single Pod could be associated with a user and more than one user can use a single Pod—for example, a family may use a single Pod, as by providing different access codes or identification means for each user. The terms "drug", "medication" and "pill" will be used in this application interchangeably. So will Server and Pod server.

Thus, the invention described in this document is a comprehensive system which:
  Identifies each tablet pill or drug, at the final target point, just before consumption,
  Is applicable to all drugs, in any form or shape
  Does not require any preparation or modification in the production line or packaging of the drug
  Does not require pharmacists' time, intervention or any modification at the point of vending
  Is easy to use
  Evaluates in real time any patient sensitivities or possible drug interactions in accordance with a patient's clinical information
  Communicates back with the patient and/or his/her care giver
  Alerts a patient and/or care provider regarding any deviation from the planned drug schedule
  Enhances economics of drug use
  Collects detailed information about the exact ways users take drugs, together with exact identification of each drug taken. Thus, this invention may assist drug safety authorities (such as the FDA) in evaluating benefits and hazards of new drugs, after the drug has been released for marketing—contributing to public health and safety.

BRIEF DESCRIPTION OF THE DRAWING FIGURES

The invention will now be described in greater detail with reference to the preferred embodiments illustrated in the accompanying drawings wherein.

DETAILED DESCRIPTION OF THE INVENTION

The present invention pertains to a system and method for managing patient care associated with a prescribed drug regimen. The system includes modules for performing identification of a drug before it is taken by a user, comparing it to known drugs, verifying whether the user has a sensitivity to the drug or if an adverse drug interaction could occur, in accordance with the user's clinical information.

Figure 1:
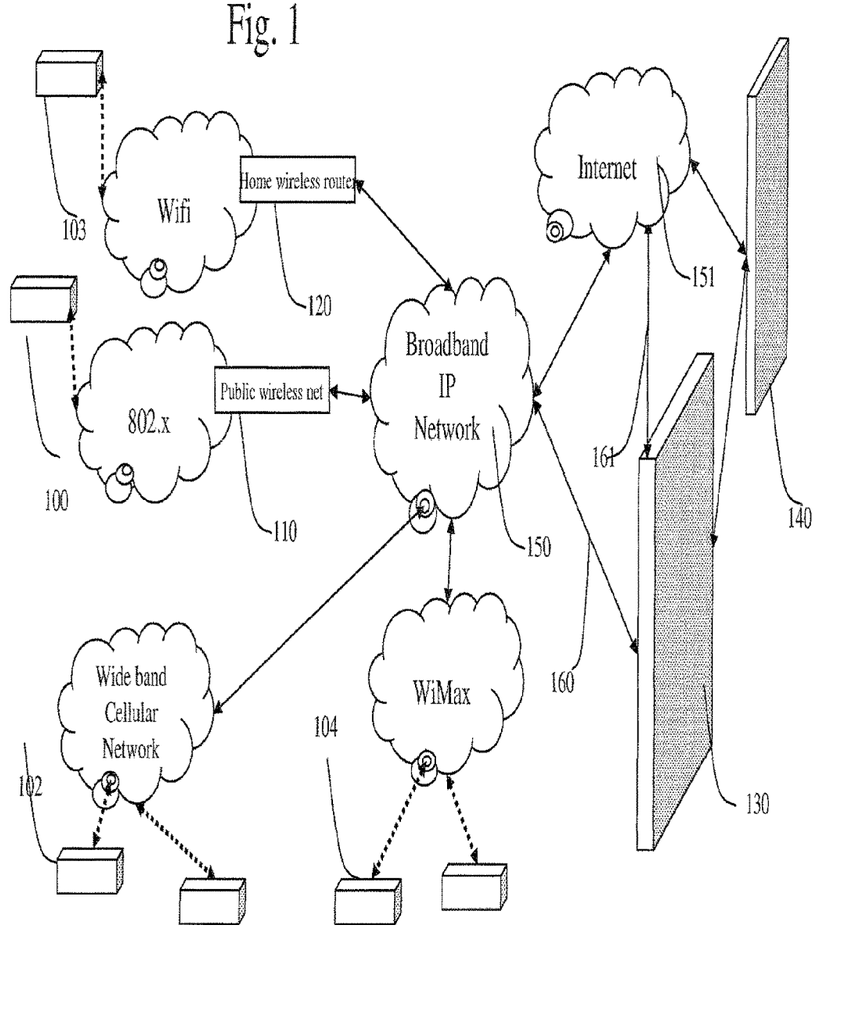
FIG. 1 depicts the overall design of a system in accordance with a preferred embodiment of the invention.

FIG. 1 illustrates a system architecture overview and several possible implementations of preferred embodiments of the invention. Pod 100 establishes connection to a server via a data link. According to a preferred embodiment, Pod 100 is connected to a wireless network, for example an IEEE 802.11n wireless IP network, and via a router 110 to a backbone broadband IP network 150. From the IP network 150, data is exchanged between Pod 100 and Pod Server 130. The data can be routed either via public internet 151, or via a private network or a private peering arrangement 160.

Once turned on, Pod 100 searches for a network to join. When a connection to the network is established, Pod 100 sends registration information to Pod server 130 via the network. The Pod server may be identified by a pre-set DNS name or pre-set global IP address, already stored within each Pod, or in any other suitable manner.

According to one embodiment of the invention, Pod 103 is located at the user's home, and connected to Pod Server 130 via a home network by known data networking links, in a similar manner to that in which a common Personal Computer (PC) communicates with servers over the Internet.

According to one embodiment of the invention, a Pod 102 can use cellular IP communications capabilities and protocols, such as GPRS, to connect to Pod Server 130, and a Pod 104 can use a wide-area wireless broadband network, such as WiMAX, for connecting to the Pod server.

Pod Server 130 is connected to Internet 151 or to IP network 150 via broadband links 161 or 160, respectively. In order to optimize the solution for traffic originating from multiple Pods, or due to geographic constraints, multiple Pod Servers can be used. Optionally, a load balancer, a firewall and other known means (not shown), that are utilized by web sites to balance traffic and protect against hackers' attacks, that are used by Internet server centers, can be used to optimize data flow to and from the Pods.

Thus, the present invention serves as a personal or domestic drug verification system that encompasses drug identification, communication links, analysis, and warning system. One identification system, utilizing images of the drug, is described herein, although other identification systems, such as Infra-red or laser-based chemical analysis, and so forth, can alternatively be integrated into the system.

In one embodiment, the Pod includes a housing defining a drug path for receiving a drug to be identified, one or more sensors in the housing for sensing and recording selected characteristics of a drug in the drug path, means for transferring the recorded characteristics to a Pod server for analysis, means for receiving analyzed data of the recorded characteristics, and a display for displaying the received data. According to one embodiment of the invention, the Pod server includes an analysis module including a medical database storing selected characteristics of as many drugs as possible, and a processor for comparing the sensed characteristics of the drug to be identified with characteristics of the drugs in the database, so as to identify the drug. The processor may also be enabled to provide an indication of potential drug interactions.

Figure 2:
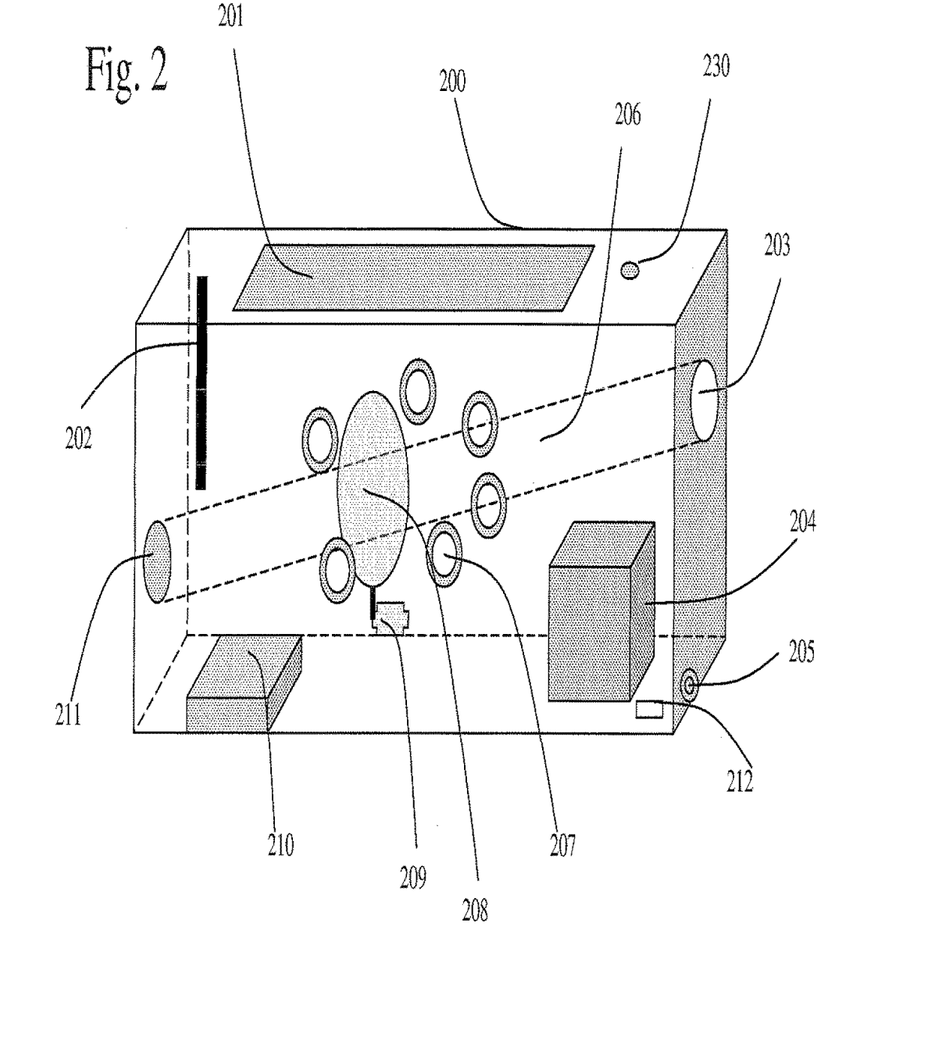
FIG. 2 depicts the basic structure of a Pod according a preferred embodiment.

FIG. 2 illustrates a Pod 220 according to a preferred embodiment of the invention. In this embodiment, the sensors include devices for capturing images of the exterior of the drug so as to permit analysis of size, color, markings, etc. Pod 220 includes a housing 200, at least one, and preferably a plurality of cameras 207, drug retaining elements, here shown as a gating element 208 and an associated gating motor 209. Pod 220 further includes a drug path 206 having at a first end a drug entry opening 203, and at a second end a drug exit 211, a power connector 205, an electronics and software module 204, a battery 210, and a display 201. Module 204 may include discrete electronics, such as hard wired circuitry, or according to a preferred embodiment, a controller controlled by software, and can further include circuitry for power management, control, etc. It is appreciated by those skilled in the art that, according to preferred embodiments of the present invention, module 204 may include communication link capabilities provided by hardware, software or a combination of both. Such a communication link can be provided by a module which is completely or partially separated from module 204.

The method of the present invention is substantially as follows. A user receives a Pod having a unique identifier, and registers the Pod with an appropriate Pod server as belonging to that user. The drug regimen of the user, including prescription drugs, non-prescription drugs, food supplements, etc., is entered into the Pod and stored there. A number of methods are available for entry of the user's data regimen, examples of which are described below. Any drug allergies or sensitivities of the user may also be entered into the Pod. If desired, the Pod can already perform a drug interaction analysis, to ensure that there are no adverse effects from the combination of drugs in the proposed drug regimen. If there are liable to be complications arising from the combination of drugs, an alert will be provided by the Pod for verification and follow-up by the user or his or her caregiver.

When a user wants to take a drug, such as a pill, either because it is the proper time to take the drug according to his prescribed regimen, or for any other reason, he places the pill in the Pod for identification. Selected characteristics of the pill will be analyzed in the Pod and/or in the pod server, and compared with characteristics of known drugs stored in a drug database. When the drug has been identified and its compatibility with the user's drug regimen has been determined, a notification is displayed for the user, who is also informed that he may take the drug or should not take the drug, for various reasons.

As an option, the Pod may be placed near, or in conjunction with, a pill dispenser, for example, MD.2 Automatic Pill Dispenser available from Epill, 70 Walnut Street, Wellesley, Mass. 02481, USA. Once a pill is dispensed by the Pill Dispenser, it is dispensed into the entry opening 203 (this can be achieved either automatically by placing the Pod next to the Pill Dispenser, or manually by the user). Then the process of pill identification and the other tasks described herein take place as described below.

According to one embodiment of the invention, the Pod provides a reminder to the user, at the appropriate time, to take a certain drug. Upon receiving confirmation from the user that the drug has been taken, the Pod will update its reminder system accordingly.

This method will now be described in detail with regard to one preferred embodiment of the invention.

When the user plans to take a pill, the user introduces a drug to Pod 220 through drug entry opening 203. Alternatively, Pod 220 may be connected to a drug dispenser, which when triggered by the user dispenses a pill or pills into opening 203. The pill moves along the drug path 206 to an analysis area. According to this embodiment, the pill is retained in the analysis area by gating element 208, which is preferably a revolving gate formed of glass, or other transparent material. Camera 207 takes a snapshot or several snapshots of the pill from one or more shooting angles. Camera 207 is shown in this embodiment as a single camera. However, preferably more than one camera may be used to capture physical characteristics of the pill from all angles. Camera 207 captures images of the pill through transparent gate element 208. It will be appreciated that camera 207 can comprise image sensors that are sensitive to the visible spectrum, for example color RGB (Red-Green-Blue) cameras which yield a color image. Alternatively, camera 207 can comprise a camera having image sensors, filters and lighting elements that produce images in the non-visible spectrum, such as near-infra-red images, which are not visible to the human eye. Infra red imaging provides an analysis of the drug's coating composition, enabling identification of the drug and also detection of counterfeit drugs.

The drug moves along the drug path 206 to an analysis area. In this embodiment, the drug is retained in the analysis area by a gating element 208, which is preferably embodied as a revolving glass gate, or a gate of another transparent material. One or more cameras take a snapshot or snapshots of the pill from one or more angles. One camera 207 is shown in this embodiment, but preferably there should be more than one camera to ensure capturing all aspects of the pill. The cameras capture images of the pill through the glass gate to obtain images of the pill from aspects that may be obscured if the gate were made of opaque material. It should be noted that the terms "camera" and "images" refer to cameras having image sensors that are sensitive to the visible spectrum, as well as to cameras having image sensor, filters and lighting elements that produce images in the non-visible spectrum, such as near-infra-red images, which are not visible to the human eye. Details of such cameras and lighting are provided in applicants' co-pending patent application entitled Apparatus and Method for Obtaining an Identification of Drugs for Enhanced Safety.

A gating motor 209, or a linear actuator or any other suitable element, can revolve the gating element 208, to permit the pill to continue its passage through the drug path 206 and get to the other end of the Pod at exit point 211. It will be appreciated that the specific activation of the gating mechanism will depend on the structure used and will be a technical choice clear to the skilled technician.

In a preferred embodiment, all the electronics, which preferably includes a programmable microprocessor, motor driver, camera controllers, memory and communication software preferably are located in the electronics and software module 204. In another embodiment of the invention, these functions may be performed by a cellular telephone handset that is coupled to the Pod via a cable. Power may be fed via power connector 205. According to one embodiment of the invention, at times when power is not available, battery 210 can provide power.

The Pod is connected to an IP or other wireless communication network via antenna 202 that may be internal to the Pod or telescoping outwards, as needed. According to one embodiment of the invention, a display 201 provides feedback to the user. Such feed-back can be, for example, the identification of the pill and additional information about that particular drug. This information can be transmitted to the Pod by Pod Server 130 from FIG. 1. According to a preferred embodiment of the invention, display 201 can be a touchscreen which enables user's input for set-up or for placing orders.

According to another preferred embodiment of the invention, a Pod may be connected, preferably wirelessly, to other or additional external sensors which measure a physical property of the user, such as a scale which measures person's weight, a blood pressure meter, a blood glucose meter and the like. The exact type of external sensor may be determined by the patient or by their care givers or service providers. Typically, the external sensor measures a physiological parameter that is controlled by the drug or drugs that patient is required to consume. By automatically reading physiological parameters at a time of consumption of drugs, or potentially at other times as well, there is a linkage between the drug, exact time of consumption, dose, and other drugs taken by the patient, to an outcome—the change in the measured physiological parameter. This may have the advantage of providing a feed-back to the patient, potentially encourage him or her to adhere and comply with their drug regimen, and provide to the physician a way of adjusting the dose or combination of drugs by looking at the outcomes. Preferably, the readout of the external sensor or sensors is communicated back to the Pod server, and may get displayed upon request of the patient or others as described in this application.

According to another preferred embodiment of the invention, screen 201 has a capability to display video. The video may be received from the Pod Server as compressed video over IP protocol, for display on display 201. The video can provide information about the use of drugs, also known as informational video. The video can also contain footage of a drug expert or technical support personnel that help the user to resolve drug-related and technical issues. According to another embodiment of the invention, Pod 220 has a video output connector that permits the content to be displayed on a television screen. The video output connector may be wired or a wireless video may be provided, as known.

According to one embodiment of the invention, an LED 2.30 can also be used to provide visual feed-back to the user. For example, such feed-back can be green, if the drug is safe to take or red, if not.

In addition, according to a preferred embodiment of the invention, an optical or RFID reader 212 can be provided to read barcode or other data encoded on drug packaging, such as syringes, or other packaging for prescription or non-prescription drugs, vitamins or food supplements.

Figure 3:
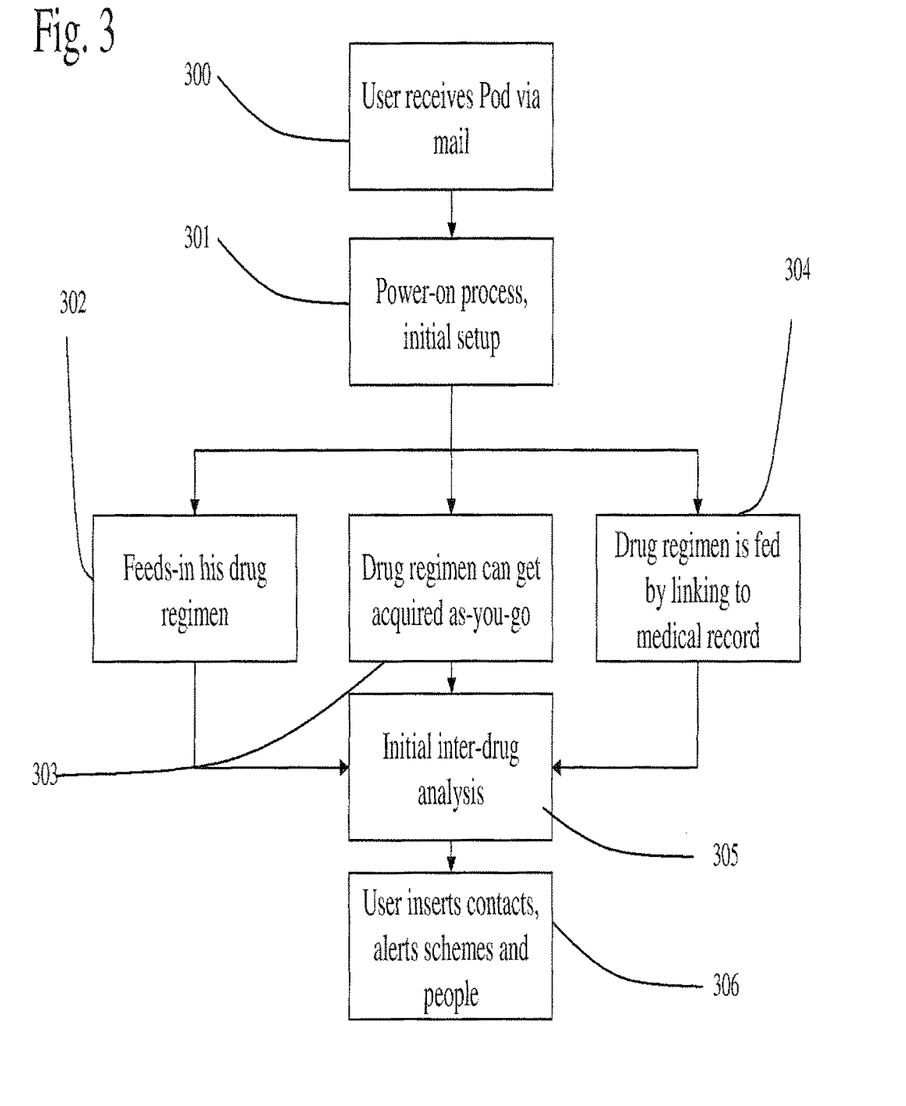
FIG. 3 is a simplified flowchart showing how a user initiates an account and feeds data to the system of the invention.

FIG. 3 is a block diagram illustration of a preferred embodiment for a set-up process. In step 300, the user receives a Pod, such as Pod 220 in FIG. 2, e.g., via mail. Each Pod has a unique ID number, such as MAC address associated with it, and this ID preferably is associated with the user account stored in Pod Server 130 in FIG. 1, at the time of ordering. In step 301, the Pod is powered up. At this stage, initial setup parameters are fed into the Pod. These parameters may include username, password, and specify a wireless or other network to connect to, including network access keys, such as WEP (Wireless Encryption Protocol) or encryption keys or codes, as required by the particular network. Another aspect of this step is to send to the Pod, via the network, the current time and date. It is preferable that, via the IP routing tables, the Pod Server will recognize the time zone the user is in for appropriate time and date information. However, this function may also be achieved utilizing alternatives, such as reception of radio waves, manual time setting, internal clock, satellite signal, Global Positioning Technology (GPS), and the like. The time, and possibly the time zone data, may be used later to alert the user to take medications on time.

Steps 302, 303 and 304 depict three alternative steps for the entry of a user's drug regimen to the Pod Server. According to a preferred embodiment of the invention, the user can select his preferred option via the display 201 in FIG. 2 on the Pod. In step 302, the user will enter his/her regimen by using a PC (Personal Computer) connected to the Internet and, through the Internet, to Web server 140 in FIG. 1. According to another embodiment of the invention, the user may enter his/her drug regimen via the touch-screen 201 in FIG. 2, by using a virtual keyboard presented on the display.

In step 303, if the user chooses to, the drug regimen can be acquired and stored as-you-go. In this case, the user starts using the Pod. Initially, no new drug will be verified by the system, and the Pod will alert the user, or his care giver, that the user is taking the wrong drug. However, while in this mode, the user can override the warning, for example, by typing in his password. By doing this, the user instructs the system to store and memorize that particular drug as part of his regimen. In addition, the user will input the number of times per day he should take this drug.

In subsequent instances where the user must take the same kind of drugs, no warning will be provided, as the drug is already stored as part of the user's regimen. Yet another alternative is depicted in step 304, where the user's drug regimen is acquired from a computerized database. Such databases may exist with the medical insurers or with pharmacy chains or can be received from a hospital or doctor's office. According to another embodiment of the invention, the user's drug regimen information can be acquired from specific databases, also known as Electronic Medical Records (EMR) or Personal Medical Records (PMR).

In step 305, the Pod server performs an initial drug to drug interaction analysis, in order to make sure there are no current conflicts between drugs taken by a patient. Step 305 may take place following either step 302 or 304, or, if step 303 was chosen for the introduction of the drug regimen, it may take place prior to 303 or after 303, as the user chooses. If desired, there can be a link to external databases to provide such analysis, although preferably such information is stored in the Pod server. In addition, some safety checks can be made to make sure the dosage is according to manufacturer's recommendations. In step 306 the user enters, via elements described in steps 302 or via the web site, details of care givers with whom the Pod Server can communicate in case an alert needs to be sent, and communication details for communication with these care givers, such as cell phone call, SMS (text message), email, instant message and the like. Step 306 can take place at any time, and is presented here in this order according to a preferred embodiment of the invention.

According to one embodiment of the invention, the system utilizes Pods that are able to take images or other data regarding drugs and transmit the information to the Pod server. In preferred embodiments, the Pods send images. It should be noted that images can be acquired using various illumination and imaging sensors, including in wavelengths that are not visible to the human eye. According to another embodiment of the invention, the Pods may send a description of images. In another embodiment, they send non-image or additional information about drugs, such as bar code or RFID code.

In an embodiment of the invention where a cell phone is utilized as a Pod, the user uses the cell phone to take a picture or pictures of a pill or pills. Then, using special software that is loaded onto the cell phone, or using the cell phone's capability of sending images to an email address, sends the image or images to a Pod server. The Pod server analyses the images and sends the drug identification and other relevant information to the cell phone in the form, of a text message or a message over IP.

In another embodiment of the invention, a purpose-specific Pod is described. The user passes a drug through the Pod. The Pod takes the drug information as described and, over a communication link, transfers the information to the Pod server. The Pod server analyses the information and transmits feedback to the Pod.

Figure 4:
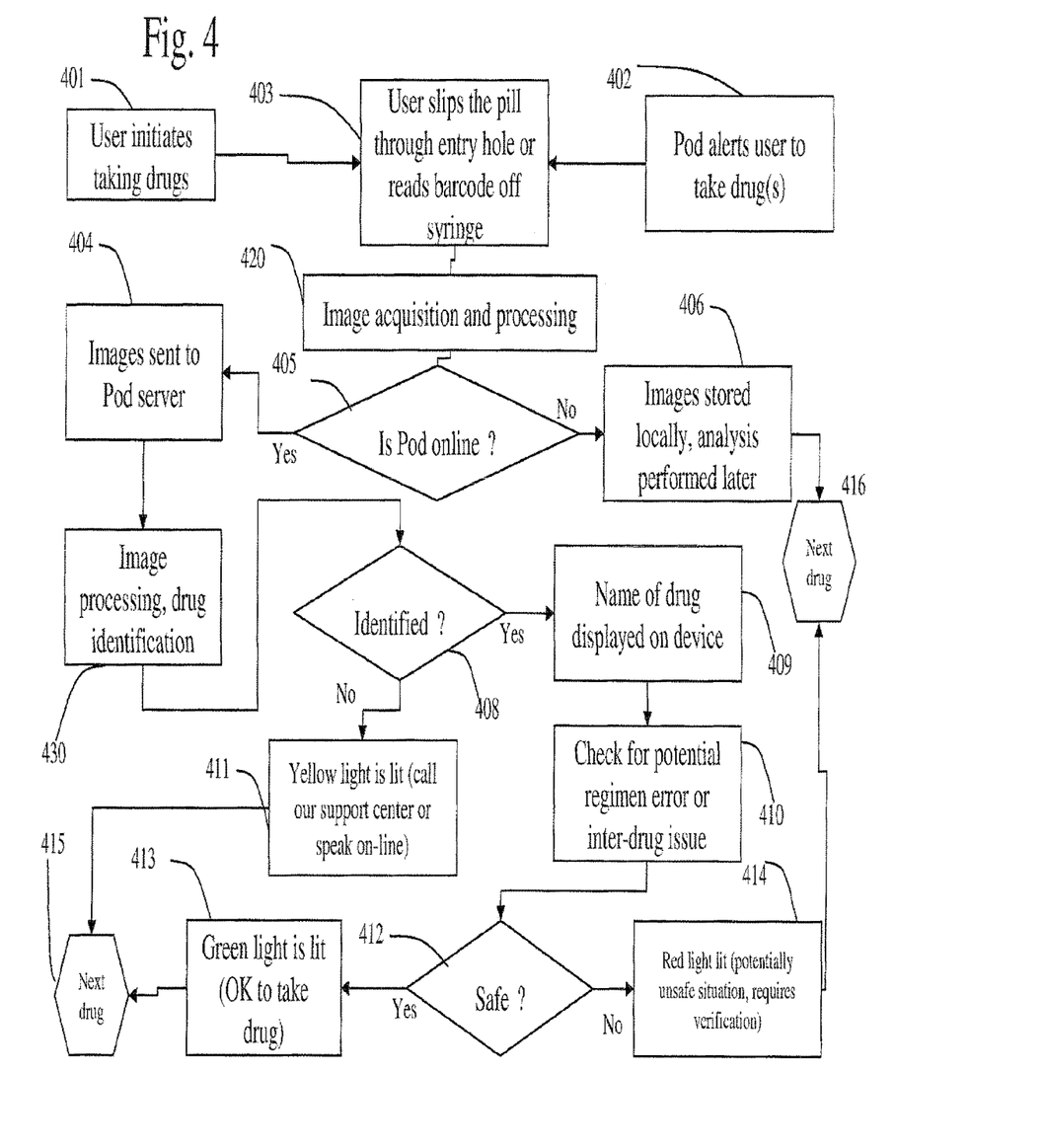
FIG. 4 is a simplified flowchart showing how a user can use the system of FIG. 1.

FIG. 4 shows a flow chart that, according to a preferred embodiment of the invention, is utilized each time the user takes a drug. In step 401, the user initiates the Pod for the process of analyzing drugs by selecting the "pill taking" menu on the device. According to another embodiment of the invention, the Pod is always on, and can automatically sense the presence of a drug, as by sampling one camera several times per second, or by using a drug entry sensor (not shown), various types of which exist commercially. One example of such a sensor is an IR (Infra Red) sensor.

As an alternative, in step 402, the Pod, knowing the time the user should take each drug, initiates an alert to the user, reminding him/her of the time and the exact drug that should be taken.

In step 403, the user slips in the drug through the entry opening (203 in FIG. 2), or reads bar code of a syringe or other drug packaging.

Step 420 is image acquisition and processing, wherein various images of the pill or the bar code or other identification element are acquired. The outcome of step 420 is a series of segmented raw images, as explained in detailed in Applicants' co-pending application cited above. The Pod now verifies that it has connectivity to the Pod Server, step 405. If it is not connected, the raw images are stored on the Pod, step 406, and will be fed to the Pod Server at a later time. Optionally, according to another embodiment of the invention, the Pod can perform image comparisons to previously stored images or extract some features out of the raw images in an attempt to verify there is no unexpected drug taken, even before the complete analysis is carried out.

This serves to expedite the transmission process by avoiding sending background image data, thus reducing the quantity of data transmitted. In step 430, image processing and analysis takes place. According to a preferred embodiment of the invention, this takes place on the Pod Server. However, according to another embodiment of the invention, processing can be performed in the Pod itself or on an attached PC or a similar computing device. At this stage, drug identification is performed and the result is transmitted back to the Pod.

If the drug was not identified, step 408, a warning signal is delivered by the Pod, step 411, by using visual signals (for example a yellow light) or audible signals, and possibly accompanied by a suitable display that suggests the user to either try passing the drug once again through the Pod, or contact customer support. Then the user can proceed to the next drug, step 415.

If the drug was positively identified, step 408, the name, and possibly dosage, of the drug is displayed on the Pod, step 409. According to another embodiment of the invention, the Pod can use digital voice capabilities to vocalize the name, dosage and, if desired, other advice. The Pod Server now performs in-depth analysis for drug-drug interaction, step 410, compliance with the drug regimen for that user in accordance with the user's clinical information, recommendations for more cost-effective generic alternatives for subsequent purchases, and similar data.

This detailed analysis is performed on the Pod server, according to a preferred embodiment of this invention; however it should be noted that the analysis can be performed on the Pod itself, or on an attached computing device, such as a PC. The in-depth analysis is done by comparing the pills the particular patient, or user is about to take, with a pre-stored drug regimen for that person, plus comparing what that patient has taken previously to known drug-drug interactions. These potentially harmful interactions can be found in commercially available drug data-bases and are updated on a regular basis by health authorities in each country, for example, the FDA in the USA.

The severity of the results is then evaluated, step 412. If the severity is high—for example, a wrong drug was detected or a potential drug-drug interaction was detected, an alarm signal is provided, step 414. This alarm signal can be any combination of light, text display or audible alarm, or any other suitable alarm. According to a preferred embodiment of the invention, a suitable text is displayed on the display of the Pod, explaining the meaning of the alarm. According to another embodiment of the invention, the Pod will not let the drug go through, by not releasing revolving gate 208 in FIG. 2, or blocking the release of the drug or drugs if the entry/exit mechanism is different. The drug, in this case, will be released only by a conscious action of the user, such as pressing a special button or selecting a special menu option. The situation described in step 414 can be resolved by either the user input, which acknowledges the error status as described, or, according to another embodiment of the invention, by contacting a support center that can release the drug by issuing a command remotely via the Pod Server. The user then can decide whether he/she should take the drug regardless, or contact a physician or pharmacist for further advice.

Once processing of a drug is completed, the Pod is ready to process the next drug, step 416. If there are no more drugs to take, the Pod resets itself back to the initial state, either automatically, for example, if it does not sense activity within a pre-determined timeout, such as 5 minutes, or, according to another embodiment of the invention, waits for a reset button or a start button to be pressed to go to the initial state.

If the drug is found to be safe, a safe indication light is lit, step 413, and the controller lets the drug exit the Pod, as by commanding motor 209 in FIG. 2 to revolve gate 208 in FIG. 2, effectively allowing the drug to roll out through drug exit 211 in FIG. 2. The user will take the drug or drugs, and move on to the next drug or to an initial state, as described.

Figure 5:
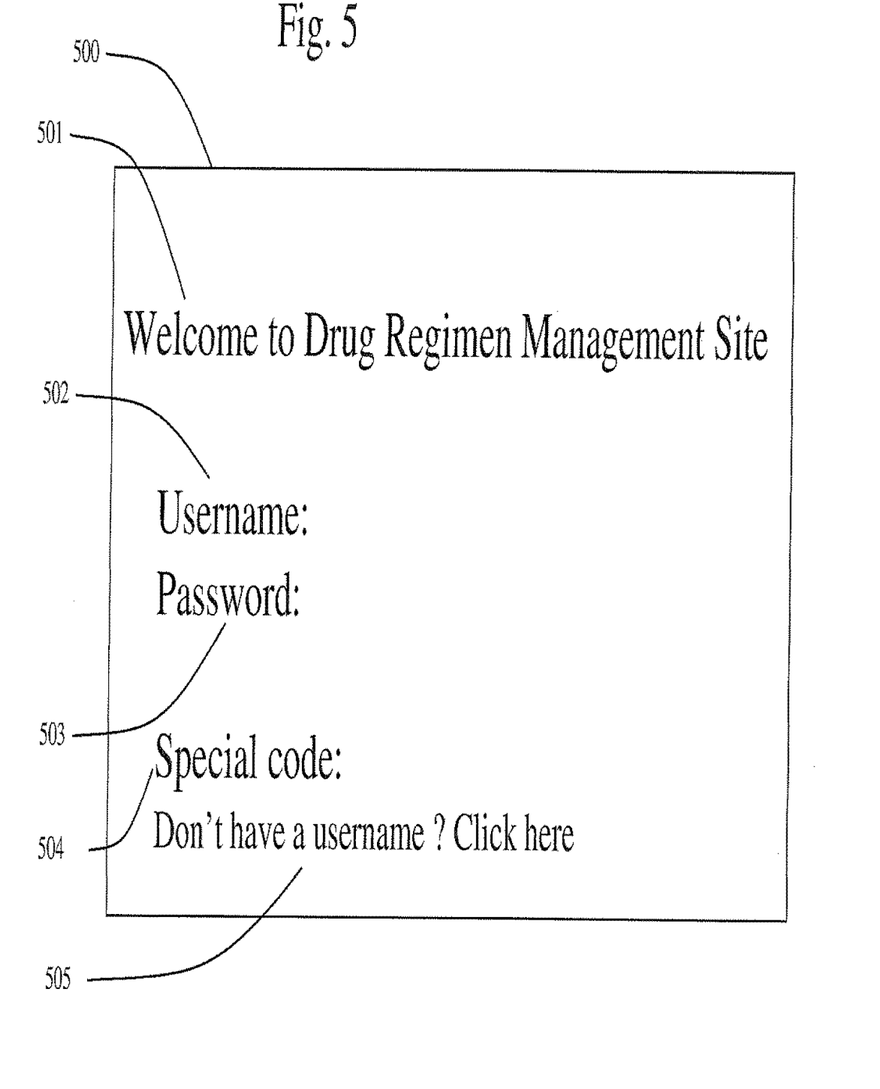
FIG. 5 is a sample front page of the web service according to a preferred embodiment.

FIG. 5 is an example of a web page of an interactive web service, according to one embodiment of the invention. This screen will be presented when a user, using any web-enabled device, such as a PC or cellular phone, accesses the web server. According to another embodiment of the invention, this screen can be presented on the Pod display for enabling similar capabilities. If such an implementation is chosen, the Pod will need a keyboard connected to it via an appropriate interface, such as USB, or a touch-screen display or a similar input unit, for providing the user's input to the Pod.

Item 501 is a welcome message, possibly accompanied by some security measures to enhance the security of the site. In items 502 and 503, the user is requested to input his or her unique username and password, as is known in Internet practice. In item 504, according to a preferred embodiment of the invention, there is a field for entering a code that is presented on the Pod screen. This code is sent to the Pod by the Pod Server when the user enters the screen or web page 500, as follows. The web browser sends the Web Server the user name that is stored on the PC, typically as a cookie, or using similar known Internet practice. Following that, the Web Server instructs the Pod Server to send a unique, randomly selected code to be displayed on the Pod screen. The user should copy this code into the web site interface 500, in field 504. This creates another layer of security and enhances the overall safety of the system described herein.

If the user does not have a user name yet, he or she must select field 505. The user will be asked for details for authentication in order to create an account. According to a preferred embodiment of the invention, the user's account will be generated automatically when the user orders a Pod. According to yet another embodiment of the invention, the Pod may be sold in a retail store or on a retail web site, and the account will be generated on-line after the Pod is delivered, as by clicking on field 505, as described.

Figure 6:
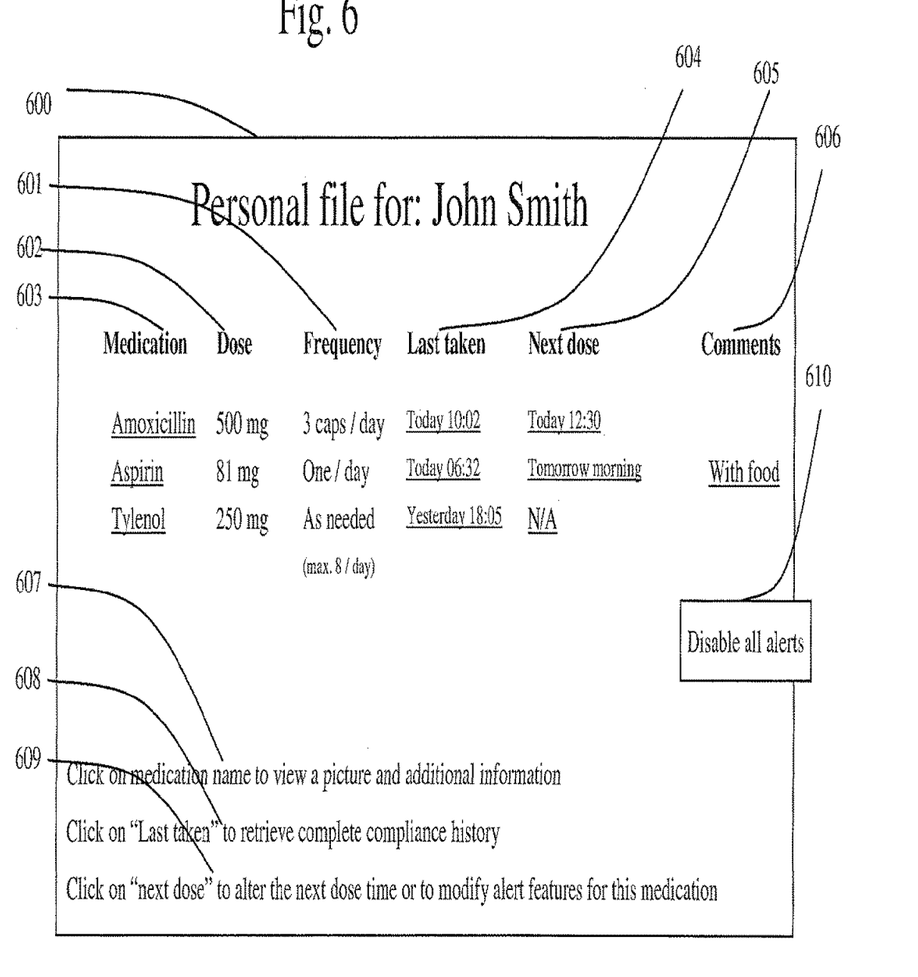
FIG. 6 is a sample page showing user data that is updated in real-time in accordance with a more preferred embodiment of the invention.

FIG. 6 presents a personal file web display 600, according to a preferred embodiment of the invention. This screen is presented to the user after the user has logged in to the Web server, as described in FIG. 5. A column headed by column header 603 shows the drugs that are on file in the Pod for this user. According to a preferred embodiment of the invention, the user can click on each entry in this column and display additional information about the drug. Such information may include a picture of the pill, or a barcode for a syringe, explanation about the activity of the drug, indications, contraindications, known drug-drug interactions with other medications or with food or with food additives, how the drug should be used, normal dosage range, what to do in case of excess dose, common side effects, history of drug taking, compliance graph, and the like. According to one embodiment of the invention, a banner 607 is displayed to encourage users to read this additional information.

Column 602 presents, for each drug, the dose this user must take. This information, like all the other information on this page, is preferably taken from a database that is maintained and updated on an on-going basis by the Pod server and, in some cases, by the Web server. Column 601 shows the frequency of taking this drug, for example, three pills per day.

Column 604 displays the last time this drug was taken by the user. Since the Pod provides feedback to the Pod server each time any drug is taken, the Pod server maintains detailed consumption records in a database, and this information can be retrieved by the Web server for display and review, both by the user, as shown in this figure, and also by a care giver or the pharmaceutical company that produces the drug, for follow up and research purposes. Known security and privacy measures need to be taken to ensure that only authorized people or entities will be able to access this data. According to one embodiment of the invention the user can click on this data field and view his consumption history. Banner 608 can direct the user to do so, but other known user interface graphic elements, such as a bubble that pops up when the pointer is over the data field or other known Internet interface methods, can be applied here.

Field 605 shows the time to take the next dose. As the drug regimen is stored in the database maintained by Pod server, the system can automatically calculate the time for the next dose of that particular drug. By clicking on this data field, the user can override the next pre-set time, and modify alert techniques which the system will use to notify both the user and, optionally, a care giver if this drug was not taken on or around the predicted time.

In column 606, there are particular comments about the medication. According to one embodiment of the invention, the user can click on an item in this list to modify or personalize the comment. According to another embodiment of the invention, the comment will be displayed on the Pod at the time it identifies this particular medication, to remind the user about special precautions or instructions for this particular medication.

A button 610 is provided in this screen, according to a preferred embodiment of the invention, in order to enable the user to temporarily block all alerts. This is useful when, for example, the user is planning to go on a trip and may not be able to use the Pod for hours or days. If the user selected this option, the writing on this button is changed to "enable" so the user, upon returning, will be able to re-enable the alert function. Known error processing techniques, such as a time out after which alerts will be re-enabled, scheduled re-enablement, or automatic re-enablement the next time the user logs in can also be implemented.

According to another embodiment, additional information, such as help lines 607 or 609, may exist on the page, as well as additional elements, such as advertisements or promotional information, as is customary on web pages.

Figure 7:
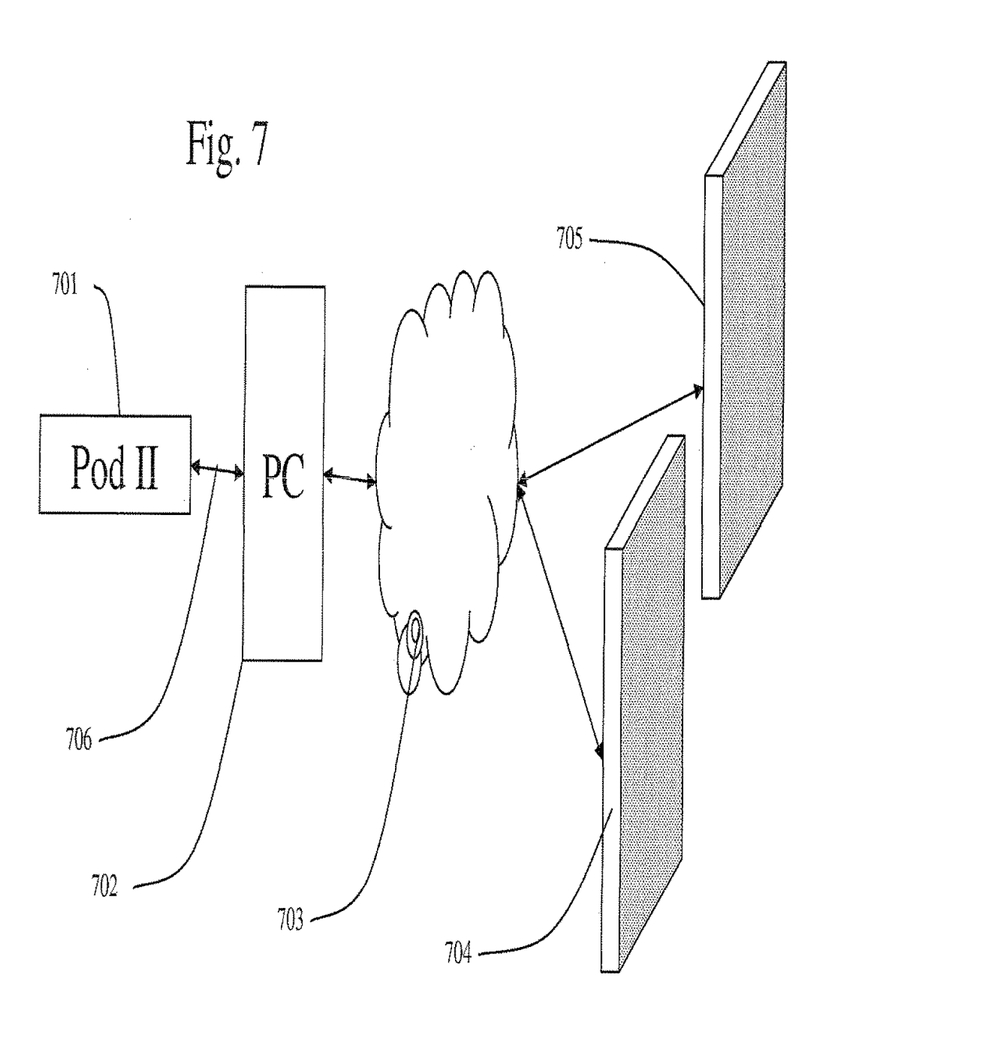
FIG. 7 is a drawing of an embodiment of the system in which a Pod is connected to a personal computer via a suitable link.

FIG. 7 depicts another embodiment of the invention. According to this embodiment, a Pod 701 contains only minimal electronics, which may bring its manufacturing cost down. Instead, or in addition, Pod 701 is connected to a personal computer (PC) 702 via any suitable link 706. According to one embodiment of the invention, this link may be either USB or wireless Bluetooth. A possible benefit of the link to a PC is to eliminate the need for power, as power can be provided over the USB cable. PC 702 must run appropriate software that communicates both with Pod 701 and with Pod Server 704 via a communication network 703. Such communication network may be the Internet. The functions of the PC software may be similar to those described for the Pod Server. The PC is also connected via the Internet or a communication network 703 to a web server 705.

It is a particular feature of the invention that the system utilizes substantially direct evidence of drug taking, rather than indirect evidence, as in the prior art. According to the invention, the Pod examines the actual pill, immediately prior to its consumption and, from that information, the system determines which drug is taken. Prior art solutions monitor when a pill container has been opened, but cannot tell if zero, one, or more pills were actually taken out.

While the invention has been described with respect to a limited number of embodiments, it will be appreciated that many variations, modifications and other applications of the invention may be made. It will further be appreciated that the invention is not limited to what has been described hereinabove merely by way of example. Rather, the invention is limited solely by the claims which follow.

The invention claimed is:

1. A system for identifying a pill comprising:
at least one electronic device (Pod), each Pod is a personal electronic device coupled to or having a sensor configured to sense and record an image of the pill, and the Pod configured to extract at least one visual characteristic of the pill by scanning segments of the image to detect a boundary of the pill, and the Pod is configured to communicate the visual characteristic to a Pod server interactively;
a data communication network configured to transfer the recorded visual characteristic to a Pod server configured to analyze the characteristic, and the Pod server is coupled by a data communication link to the Pod, the Pod server comprises an analysis unit having a drug characteristics database or a link to an external database having such information, and the drug characteristics database comprises visual characteristics of a plurality of drugs; and
a processor configured to receive the visual characteristic of the pill and compare the characteristic with characteristics of drugs in the drug characteristics database, and identify the pill; the Pod personal electronic device configured to further receive analyzed data and information comprising the identity of the pill from the Pod server; and
a display coupled to or within the Pod personal electronic device, the display configured to display the identity of the pill, or the Pod configured to deliver a visual or an audible warning signal if the pill is not identified, and the personal electronic device configured to notify a user of an unsafe situation, an inter-drug interaction, or a verification requirement, until the situation, the interaction, and the requirement is resolved by user input.

2. The system according to claim 1, wherein the visual characteristic is selected from at least one of the group consisting of: size, shape, color, markings, and images analyzed in a non-visible spectrum.

3. The system according to claim 1, wherein the sensor captures images of the visual characteristic of the pill; the drug characteristics database comprises images of a plurality of drugs that are pills; and the processor compares an image of the characteristic of the pill with the images in the drug characteristics database.

4. The system according to claim 1, wherein the sensor is a camera.

5. The system according to claim 1, wherein the display is on the POD.

6. The system according to claim 2, wherein the non-visible spectrum is near-infrared light.

7. The system according to claim 1, further comprising a personal computer coupled to the POD by a data communication link.

8. The system according to claim 1, further comprising a personal computer coupled to the POD server by a communication link.

9. The system according to claim 7 or 8, wherein the PC comprises at least one selected from the group consisting of: a device for transferring data, a device for receiving data, software for communicating with the Pod and with the Pod Server, and a display.

10. The system according to claim 1, wherein the POD further comprises a user interface.

11. The system according to claim 1, wherein the POD comprises a device that obtains an output signal corresponding to the sensed characteristic of the pill, wherein the device sends the output signal to the processor.

12. The system according to claim 1, wherein the Pod is a cellular telephone.

13. The system according to claim 1, wherein the Pod server is embedded within the personal electronic device.

14. A method for identifying a pill comprising:
sensing and extracting by an electronic device (Pod) a visual characteristic from an image of at least one pill by scanning segments of the image to detect a boundary of the pill, and the Pod is a personal electronic device having a sensor;
transmitting the characteristic to a Pod server by the personal electronic device, the Pod server comprises an analysis unit having a processor that compares the sensed characteristic of the pill with characteristics of a plurality of known drugs to identify the pill, the Pod displaying: identity of the pill on a display coupled to or within the personal electronic device; or the Pod delivering a warning signal if the pill is not identified by the analysis unit; or if the Pod is not connected; or a process of transmission and background image data reduces a quantity of data transmitted, or delivering a warning if the pill is identified as a wrong drug or as an unexpected drug; and
notifying a user by the personal electronic device of an unsafe situation, an inter-drug interaction, or a verification requirement, and resolving the situation, the interaction, or the requirement by input from the user.

15. The method according to claim 14, wherein the characteristic is optical or visual.

16. The method according to claim 14, wherein the characteristic is selected from the group of: size, shape, color, markings, and images analyzed in a non-visible spectrum.

17. The method according to claim 16, wherein the non-visible spectrum is near-infrared light.

18. The method according to claim 14, wherein identifying and displaying identity of the pill further comprises transmitting a message to the POD selected from a voice message, a text message, and a video message or a combination thereof.

19. The method according to claim 14, further comprising alerting an individual of the identity of the pill.

20. The method according to claim 14, wherein sensing comprises using a camera to obtain images of the visual characteristic of the pill, and sending the images to an email address corresponding to the POD server.

21. The method according to claim 14, wherein the POD is a cellular telephone.

22. The method according to claim 14, wherein the warning signal comprises at least one of a visual and audible signal.

23. The method according to claim 15, wherein the pill is not identified and the warning signal further comprises instructing the user to try passing the pill again through the Pod or contacting customer support.

* * * * *